US010223557B2

(12) United States Patent
Malcolm

(10) Patent No.: US 10,223,557 B2
(45) Date of Patent: Mar. 5, 2019

(54) ERGONOMIC HELD WEIGHT UNIT

(71) Applicant: Christian Malcolm, Thousand Oaks, CA (US)

(72) Inventor: Christian Malcolm, Thousand Oaks, CA (US)

(\*) Notice: Subject to any disclaimer, the term of this patent is extended or adjusted under 35 U.S.C. 154(b) by 31 days.

(21) Appl. No.: 15/188,048

(22) Filed: Jun. 21, 2016

(65) Prior Publication Data

US 2017/0361146 A1     Dec. 21, 2017

(51) Int. Cl.
*A63B 21/00* (2006.01)
*A63B 21/02* (2006.01)
(Continued)

(52) U.S. Cl.
CPC .......... *G06K 7/10366* (2013.01); *A61B 5/681* (2013.01); *A63B 21/028* (2013.01);
(Continued)

(58) Field of Classification Search
CPC .......... A63B 21/0004; A63B 21/00058; A63B 21/00061; A63B 21/00065; A63B 21/00069; A63B 21/00072; A63B 21/00185; A63B 21/06; A63B 21/0604; A63B 21/065; A63B 21/068; A63B 21/072; A63B 21/0722; A63B 21/0724; A63B 21/0726; A63B 21/0728; A63B 21/075; A63B 21/08; A63B 21/4017; A63B 21/4019; A63B 21/4021; A63B 21/4023; A63B 21/4025; A63B 21/4027; A63B 21/4033; A63B 21/4035; A63B 21/4039; A63B 21/4043; A63B 23/12; A63B 23/1209; A63B 23/1245; A63B 23/1281; A63B 23/14; A63B 23/16; A63B 24/0003; A63B 24/0021; A63B 24/0062; A63B 24/0075; A63B 24/0087; A63B 2024/0028; A63B 2024/0031; A63B 2024/0034; A63B 2024/0053; A63B 2024/0065; A63B 71/0619; A63B 71/0622; A63B 71/0686;
(Continued)

(56) References Cited

U.S. PATENT DOCUMENTS 3,542,363 A \* 11/1970 Smith ................... A63B 23/16
482/49
4,351,526 A    9/1982 Schwartz
(Continued)

OTHER PUBLICATIONS

Kinsey, C., "What Are the Effects of Walking With Weights?", 2015, retrieved from http://www.livestrong.com/article/345267-what-are-the-effects-of-walking-with-weights/, pp. 1-4.

*Primary Examiner* — Gary D Urbiel Goldner
(74) *Attorney, Agent, or Firm* — One LLP; Joseph K. Liu

(57) ABSTRACT

Hand held weight units of light weight manufactured as a solid unit, a shell unit with core insert combinations or modular units with interlocking ends. Shell units with core inserts and modular interlocking units allow for the changing of held weight by inserting or removing inserts or by locking or unlocking of modular weight unit sets creating varying held weight. The weight units are primarily used with upper body exercises during aerobic exercises in the home, outdoors, or in a gym setting such as walking or running to vary the intensity of workout during use.

6 Claims, 16 Drawing Sheets

(51) Int. Cl.

| | | |
|---|---|---|
| *A63B 21/065* | (2006.01) | |
| *A63B 69/00* | (2006.01) | |
| *G06K 7/10* | (2006.01) | |
| *G09B 19/00* | (2006.01) | |
| *G09B 5/02* | (2006.01) | |
| *A61B 5/00* | (2006.01) | |
| *A61B 5/024* | (2006.01) | |
| *A61B 5/11* | (2006.01) | |

(52) U.S. Cl.
CPC ........ *A63B 21/065* (2013.01); *A63B 21/4039* (2015.10); *A63B 69/0028* (2013.01); *G09B 5/02* (2013.01); *G09B 19/0038* (2013.01); *A61B 5/024* (2013.01); *A61B 5/1121* (2013.01); *A61B 5/4866* (2013.01); *A61B 5/6806* (2013.01); *A61B 2503/10* (2013.01); *A63B 2209/08* (2013.01); *A63B 2220/40* (2013.01); *A63B 2220/803* (2013.01); *A63B 2225/50* (2013.01); *A63B 2225/54* (2013.01); *A63B 2225/68* (2013.01); *A63B 2225/682* (2013.01); *A63B 2225/685* (2013.01); *A63B 2225/687* (2013.01); *A63B 2230/06* (2013.01); *A63B 2230/75* (2013.01)

(58) Field of Classification Search
CPC ...... A63B 2071/065; A63B 2071/0658; A63B 2071/0661; A63B 2071/0663; A63B 2017/0675; A63B 2071/0677; A63B 2071/068; A63B 2071/0683; A63B 2071/0694; A63B 2220/12; A63B 2220/13; A63B 2220/14; A63B 2220/16; A63B 2220/17; A63B 2220/30; A63B 2220/31; A63B 2220/34; A63B 2220/35; A63B 2220/36; A63B 2220/40; A63B 2220/44; A63B 2220/51; A63B 2220/52; A63B 2220/58; A63B 2220/62; A63B 2220/80; A63B 2220/803; A63B 2220/805; A63B 2220/83; A63B 2220/833; A63B 2220/836; A63B 2225/09; A63B 2225/093; A63B 2225/20; A63B 2225/50; A63B 2225/52; A63B 2225/54; A63B 2320/75; A63B 2230/755

See application file for complete search history.

(56) References Cited

U.S. PATENT DOCUMENTS

| | | | | |
|---|---|---|---|---|
| 4,929,211 A * | 5/1990 | Resnick | ............. | A63B 23/16 446/14 |
| 5,180,352 A * | 1/1993 | Sreter | ............. | A63B 21/072 482/1 |
| 5,250,014 A | 10/1993 | Chang | | |
| 5,297,541 A * | 3/1994 | Hensey | ............. | A63B 23/16 482/47 |
| 5,530,967 A * | 7/1996 | Cielo | ............. | A63B 71/143 2/16 |
| 5,800,311 A * | 9/1998 | Chuang | ............. | A63B 21/22 482/2 |
| 5,820,523 A * | 10/1998 | Zemer | ............. | A63B 23/16 482/49 |
| 5,947,871 A * | 9/1999 | Gilcrease | ............. | A63B 23/16 482/127 |
| 6,042,508 A | 3/2000 | Clem et al. | | |
| 6,142,918 A * | 11/2000 | Liu | ............. | A63B 21/072 16/430 |
| 7,025,713 B2 | 4/2006 | Dalebout et al. | | |
| 7,083,553 B2 * | 8/2006 | Leon | ............. | A63B 21/072 482/106 |
| 7,379,770 B2 | 5/2008 | Szeto | | |
| 7,908,672 B2 | 3/2011 | Butler | | |
| 8,579,827 B1 | 11/2013 | Rulkov et al. | | |
| 8,684,893 B2 | 4/2014 | Tang | | |
| 8,992,396 B2 | 3/2015 | Wang | | |
| 9,132,316 B2 | 9/2015 | Lima et al. | | |
| 9,237,855 B2 | 1/2016 | Hong et al. | | |
| 9,682,272 B2 * | 6/2017 | Januszek | ............. | A63B 21/0724 |
| 2003/0022766 A1 * | 1/2003 | Gates | ............. | A63B 21/0606 482/92 |
| 2003/0100408 A1 * | 5/2003 | Chuang | ............. | A63B 21/22 482/44 |
| 2003/0139256 A1 * | 7/2003 | Chuang | ............. | A63B 23/14 482/44 |
| 2004/0063546 A1 * | 4/2004 | Chuang | ............. | A63B 21/22 482/45 |
| 2004/0198557 A1 * | 10/2004 | Davis | ............. | A63B 21/028 482/49 |
| 2005/0101440 A1 * | 5/2005 | Chuang | ............. | A63B 21/22 482/45 |
| 2005/0107218 A1 * | 5/2005 | Chuang | ............. | A63B 23/14 482/45 |
| 2005/0113214 A1 * | 5/2005 | Chuang | ............. | A63B 21/225 482/44 |
| 2006/0046900 A1 * | 3/2006 | Chuang | ............. | A63B 21/0608 482/44 |
| 2006/0229174 A1 * | 10/2006 | Bonutti | ............. | A63B 21/0004 482/111 |
| 2007/0167266 A1 * | 7/2007 | DeVall | ............. | A63B 43/00 473/505 |
| 2007/0179031 A1 * | 8/2007 | Chang | ............. | A63B 21/06 482/108 |
| 2007/0207899 A1 * | 9/2007 | Chuang | ............. | A63B 21/22 482/45 |
| 2008/0026915 A1 * | 1/2008 | Chuang | ............. | A63B 21/22 482/44 |
| 2008/0058166 A1 * | 3/2008 | Chuang | ............. | A63B 21/22 482/44 |
| 2008/0268278 A1 * | 10/2008 | Walsh | ............. | A63B 21/06 428/600 |
| 2010/0048359 A1 * | 2/2010 | Chuang | ............. | A63B 21/22 482/44 |
| 2010/0130314 A1 * | 5/2010 | Von Der Gruen | ...... | A63B 63/00 473/570 |
| 2011/0009713 A1 * | 1/2011 | Feinberg | ............. | A61B 5/0205 600/301 |
| 2012/0244969 A1 * | 9/2012 | Binder | ............. | A63H 33/18 473/570 |
| 2013/0109540 A1 * | 5/2013 | Chuang | ............. | A63B 71/06 482/45 |
| 2013/0178336 A1 * | 7/2013 | Chuang | ............. | A63B 71/0622 482/8 |
| 2013/0310224 A1 * | 11/2013 | Chuang | ............. | A63B 23/14 482/45 |
| 2014/0155226 A1 * | 6/2014 | Chuang | ............. | A63B 23/14 482/46 |
| 2014/0200115 A1 * | 7/2014 | Chuang | ............. | A63B 23/14 482/8 |
| 2014/0373244 A1 * | 12/2014 | Jhaveri | ............. | A63B 71/14 2/20 |
| 2014/0378278 A1 * | 12/2014 | Chuang | ............. | A63B 23/14 482/46 |
| 2015/0231445 A1 * | 8/2015 | Chuang | ............. | A63B 21/0004 482/2 |
| 2017/0361159 A1 * | 12/2017 | Malcolm | ............. | A63B 21/4039 |

* cited by examiner

ERGONOMIC HELD WEIGHT UNIT

BACKGROUND OF THE INVENTION

The present invention relates to dumbbells, adjustable dumbbells, and more particularly to light weight dumbbells or light weight adjustable hand weights having specific ergonomic shapes that allow for the centering of weight in the palm of the hand, and interlocking features that allow for the ease of combination of units during an aerobic exercise to achieve a specific desired weight and intensity of workout.

Moreover, the present invention also relates to worn devices that are intended to track heart rates, steps or strides, body movements, force and exertion of movement with held weight, and calories burned per hour through the use of: heart rate monitors, pedometers, gyroscopes, accelerators, and other sensors.

DESCRIPTION OF THE BACKGROUND

Aerobic exercise has always been an effective way to lose weight, increase physical conditioning, and maintain a healthy lifestyle. However, over time, the body adjusts to the aerobic exercise by increasing both strength and physical endurance, making the same activity easier and easier to perform. Therefore, to maintain a high level of physical exertion during aerobic exercises, weight or resistance must be added or increased over time to keep up with the body's increased physical conditioning.

Adding held weight to any aerobic activity is a great way to accomplish such addition of weight or resistance. There exists a wide variety of indoor and outdoor exercises that are made more challenging when even the smallest amount of held weight is added to the activity. Increasing the heart rate, muscle activity, and total calories burned per hour is possible with the addition of dumbbells or various methods of holding weight in the hand during physical activities.

A conventional dumbbell is intrinsically formed as a single solid unit and its weight is constant. Hence, devoted users typically possess a multitude of dumbbell sizes and shapes of different weights and, in doing so, must choose a single weight to hold during prolonged aerobic exercise. This single weight limitation poses a problem for the users doing interval upper body weight training during continuous or prolonged aerobic exercises, such as walking or running, as it forces the individual to use one weight across all upper body exercises.

A typical adjustable dumbbell system is intrinsically designed with a method of adding plates, rings, or weight segments to a center bar or grip. Hence users need to add or subtract weight segments and then lock or screw in the weight in place prior to aerobic exercise. Changing the weight during aerobic exercise would require unlocking of weight segments from the central bar or grip and adding or subtracting weight, then relocking the new desired weight into place. In doing so, the wearer must stop physical activity and make the changes to each dumbbell before resuming the activity. In addition, the typical adjustable dumbbell weight isn't practical to carry on the body during prolonged aerobic exercise and lends itself for use only within the home or gym setting where the additional weight segments are properly stored or housed on racks or in a complete set of incremental weight stacks. Hence, users must typically choose a single weight to hold during prolonged aerobic exercise which poses a problem for the users doing interval upper body weight training during continuous aerobic exercise.

Simply put, using the same held weight across many different upper body exercises or arm movements doesn't achieve the most beneficial workout when compared to alternating intensities of exercises by changing the held weight during aerobic exercises. In addition, as previously mentioned, traditional dumbbells and adjustable dumbbells are formed with a center grip bar with weight blocks attached at both ends, the larger the weight the larger the outer weight blocks or segments become. Therefore, it can be concluded that these traditional dumbbell shapes are not advantageous during aerobic activity, as they often alter the form of the exercise to limit the risk of banging the weights together or coming in contact with the body. In addition, traditional dumbbell shapes can come in contact with aerobic machines such as treadmills or step climbers during certain arm movements or motions, can get hung up or caught on headphone wires during exercise, and can hit a walking or running partner's dumbbell or body as they are swung back and forth by the holder when exercising in a group. Therefore, there exists a need for a hand held weight system in which most of the weight is centered in the palm. In addition to the single weight unit being centered in the palm of the hand, it is also most advantageous for the user that when units are joined together and held as one joined unit of increased weight and mass, there is only a limited amount of weight unit exposed on either end of the holder's hand circumference.

There may be additional benefits having the weight centered over the palm in a rounded or oval shape. *Discover Walking* and *The Walking Site* both point out that walking with hand weights or dumbbells can increase blood pressure caused by the gripping or squeezing of the weights tightly. "If an individual carries weights several days per week for an extended period of time, their blood pressure could be adversely affected. High blood pressure can lead to other serious health problems such as heart disease and an increased risk for stroke," *The Walking Site*. A rounded egg or oval shaped weight unit, with finger grips centered over the palm, can help reduce the tendency for the user to clench their fist tightly around a thin centered bar grip and thus can reduce or eliminate the risk of increasing blood pressure during aerobic activity. Therefore, when an individual chooses to walk or run with weights for the added training benefit, it is most advantageous to hold a weight that is specifically designed to be ergonomically centered in the palm of the hand and for a light gentle holding thereof during prolonged aerobic exercise. In addition to all the physical intrinsic benefits of holding a light weight that is centered in the palm of the hand, for some individuals, the ability to conceal the light weight in the center of the hand is advantageous. Some individuals perceive the holding of standard dumbbells more visible and unpleasant, causing them to feel self-conscious about exercising with held weights. Additionally, women or men with long finger nails can experience a digging in effect when gripping the small center bar of traditional dumbbells.

Individuals who use adjustable held weight during prolonged aerobic exercise to increase or decrease the intensity of their workout, will benefit greatly by tracking, monitoring, and reviewing the intensity of their work out across all muscle groups used during exercise. In addition, the data generated by tracking the held weight with specific exercises and each muscle group associated with the exercise is critical for users to review, understand, and monitor their individual progress and performance over time. Therefore, it is critical to provide this data in an easy to understand and reviewable format. In order for the user to set and achieve his or her goals of physical fitness, they must be able to comprehend which exercises performed correspond to which muscle groups and the impact of held weight.

DESCRIPTION OF RELATED ART

Hand held adjustable light weight dumbbells, gloves with encircled adjustable weight bars, or other similar light weight hand held systems are designed to increase or decrease held weight prior to an aerobic exercise and are generally known in the art. U.S. Pat. No. 4,351,526 to Schwartz, U.S. Pat. No. 5,250,014 to Chang, U.S. Pat. No. 6,042,508 to Clem, U.S. Pat. No. 7,025,713 to Dalebout, U.S. Pat. No. 7,908,672 to Butler, U.S. Pat. No. 8,684,893 to Tang, U.S. Pat. No. 8,992,396 to Wang, U.S. Pat. No. 9,132,316 to Lima, et al disclose various types of such adjustable dumbbells, gloves, or weight systems which may or may not include tracking or monitoring devices within. None of these devices, however, is satisfactory for extended aerobic exercises in which hundreds or even thousands of repetitive arm exercises are performed each with its own unique weight tolerance or desired weight associated with the required movement, muscle group, and fitness level of the user. For example, an individual of average physical conditioning can perform bicep curls while engaged in an aerobic activity such as walking, or jogging at a specific weight; however, if the individual wishes to change his/her upper body arm movement to achieve a more rounded upper body work out the weight may need to be increased or decreased to perform a new movement such as arm circles, fast jabs, shoulder presses or uppercuts. Simply using the same weight across many different upper body exercises and muscle groups isn't advantageous when trying to achieve the most beneficial workout. The most effective way to build or tone muscle groups, during prolonged aerobic exercise, is to alter the intensity of the exercise by changing the held weight across repetitions and sets of repetitions of varying exercises and muscle groups.

Therefore, there exists the need for a hand held weight system where weight units, or weight inserts can be stored on the body and easily locked or linked together during aerobic exercise to increase or decrease the intensity of held weight during upper body exercises.

In addition to the adjustable weight system, the invention also relates to worn tracking or monitoring devices that use a pedometer, accelerator, gyroscope, or other sensors to track the user's motion and physical output during exercise. These devices are generally known in the art. U.S. Pat. No. 7,379,770 to Szeto, U.S. Pat. No. 8,579,827 to Rulkov, and U.S. Pat. No. 9,237,855 to Hong, et al disclose various types of such monitoring and tracking devices. Such devices have several common and primary functions: 1. Track and display the heart rate of the wearer by the use of sensors, 2. Track and display the calories burned during activity or at rest by use of the wearer's heart rate against variables input by the user such as weight, fitness level, and age, 3. Display overall performance of an activity or exercise over time and set future goals or targets for physical activity. An example of this would be how far an individual ran during 1 hour, average heart rate during the time, high and low heart rate achieved during the activity, and how many calories were burned during that activity.

Although the above mentioned devices and those similar to them accurately track and display the physical activity and exertion of the wearer including: heart rate, calories burned, number of steps, strides, or cycles and potentially upper body movements, none track and monitor the above mentioned physical activity performed in combination with varying held weight and with upper body exercises during prolonged aerobic activity.

Therefore, there exists the need for either: 1. A manual or audio feature on the tracking device (smart watch, smart phone, or other device) that allows the wearer to input the variable held weight into a tracking device during prolonged aerobic exercise to accurately track held weight with upper body exercises, or 2. An automatic tracking sensor system that is embedded into a worn monitoring device, smart phone, smart watch, etc. that can read, monitor and track the variable combinations of held RFID (Radio Frequency Identification) tagged or chipped weights used with upper body exercises during aerobic activity such as walking, jogging, swimming, running, yoga, stationary exercise or stretching.

SUMMARY OF THE INVENTION

The present invention eliminates the aforesaid circumstances of the prior art. It is therefore an object of the present invention to provide a small light weight interlocking modular dumbbell or modular weight unit to allow the holder to change hand held weight with ease by simply locking and unlocking weight units during aerobic exercise. The method of locking and unlocking weight segments may use multiple means of joining two like objects together including male and female locking pins, interlocking rigid features, magnets, and any other means to join the two segments together. Examples are provided within the drawings and descriptions thereof. It is another object of the present invention to provide a small light weight unit made from either lead, cast iron, steel or any other heavy durable metal or material to meet the desired weight and shape of the weight unit. It is another object of the present invention to have the potential for an inner core and an outer core of varying metals or casted layers within the modular unit to achieve the specific weight and shape of the unit as well as create a barrier or protective layer around softer but denser metals such as lead. It is another object of the present invention to provide a RFID tracking tag/microchip or other tracking device or system thereof which is embedded within a weight unit that communicates to a smart phone, smart watch, or similar device to automatically identify the individual or combined continuous weight values during upper body movements and exercise. It is another object of the present invention to provide a modular weight unit that is centered in the palm of the hand of the holder whether it's in a singular form, combined into a set, or a shell weight unit with an insert. It is another object of the present invention to have a less expensive non-interlocking weight unit or hand dumbbell that is centered over the palm of the hand overcoming all the aforementioned shortcomings of the prior art that is intended for use during aerobic exercise with and without tracking weight tags—some individuals may benefit greatly from a palm centered weight but not need the added benefit of combined weight. For example, older individuals, individuals with disabilities, individuals new to physical activity, or individuals with injuries may only be capable of utilizing a singular solid light weight unit and not need an interlocking high intensity workout. It is another object of the present invention to utilize a palm centered weight shell with varying insert weights that may be locked therein or removed to increase or decrease weight accordingly during aerobic exercise. It is another object of the present invention to utilize motion tracking sensors such as gyroscopes and accelerators within a smart watch, or other monitoring devices that are worn on the wrist or forearm in combination with inputs from the wearer such as height to track individual upper body motion of the wearer through algorithms computing the X, Y, Z axis points (roll, pitch, and yaw), and rotational acceleration data points of each movement performed by the user. It is another object of the present invention to store, until needed, the weight units or inserts on the body during aerobic exercise. Such storage devices might include upper body vests, waist belts, arm bands, ankle bands, and any other storage system related to the ergonomic storage of weight units during aerobic exercise. It is another object of the present invention to utilize software installed on the monitoring or tracking device in which users can enter, at the beginning of exercise, the total body held weight including hand held weight and any stored weight by use of a vest, belt or other method. As the user increases or decreases hand held weight and increases or decreases stored weight on the body, the software can track the changes through communication either by the automated tag system or the less expensive manual or voice method to accurately measure both hand held weight affecting upper body movements as well as weight held on the body impacting lower body muscle groups accordingly. It is another object of the present invention to utilize the weight units as therapeutic objects during physical or occupational therapy. Small units of held weight that are centered in the hand might be more advantageous when stimulating torn or damaged muscles, tendons, or ligaments than traditional dumbbells that require a greater grip or squeezing effect to hold and perform therapeutic movements. It is another object of the present invention to use the light weight palm centered units in high frequency movements to increase the intensity of exercise during both stationary activity or aerobic exercise, such as boxing, martial arts, or other fast hand movements. It is another object of the present invention to use the light weight palm centered units in low frequency, slow movements to increase the intensity or effectiveness of the activity—stretching, yoga, meditation, and tai chi are all examples of low frequency, slow movement activities that can benefit with the addition of palm centered weights. It is another object of the present invention to utilize light weight hand straps, VELCRO™ hook-and-loop fastener wraps, neoprene grips, rubber flexible grips, rubber gel filled grips, or gloves to hold the weight unit centered in the palm during high speed arm movements, included the aforementioned activities and additional arm movements generated from activity such as sprinting or swimming, when typically, the hand is not generally closed around the weight unit. It is another object of the present invention that the weight unit can be coated in a resilient plastic, neoprene, or rubber material to ensure the proper gripping or holding thereof during aerobic exercise, decrease the slipping effect with the accumulation of sweat build up during activity, allow for the easy cleaning of the weight units with soap and water after use, protect the weight unit chip or tag from damage during use or cleaning, and to protect the weight from getting scratched or damaged if dropped or hit by another object. It is another object of the present invention to offer a sweat resistant cover or wrap made of resilient plastic or rubber in various colors or prints to add gripping points as well as marketing or branding opportunities including: company logos or slogans, University colors and logos, colors symbolizing special events such as the Susan Komen Race for the Cure, and any other print or color that relates to individuals in a special or meaningful way. It is another object of the present invention that the data collected from the gyroscope and accelerator unit, in conjunction with the continuous held weight values, be visible to the user either on the smart monitoring device itself or uploaded to a smart phone, tablet, laptop, or computer in such a way that it is easy to read and understand. Such a format would include: graphs, charts, total arm movements by category and muscle group, total pounds lifted per hour, total pounds lifted, total pounds lifted per muscle group, total pounds lifted per individual exercise, etc. It is another object of the present invention that the total data generated from the gyroscope and the accelerator, in conjunction with the varying held weight, shall provide an overall analysis displayed on either the smart monitoring device itself or uploaded to a laptop, tablet, phone, or computer depicting an animated male or female digital body display with the intensity of the exercises and the muscle groups used to perform said exercises identified by color of intensity and performance. For example, if an individual performed mostly all bicep curls during their aerobic activity, the digital body would show red in the bicep muscle for high intensity, yellow in the forearm muscle group for medium intensity, and green for low performance or intensity in the remaining upper body muscle groups. Furthermore, by rotating the digital body with the swipe of a finger on the display window, the digital body rotates to show muscle groups located on the individual's back to complete the entire upper body muscle groups. The digital body may also include lower body muscle groups, utilizing data generated from the sensors to track muscle activity during aerobic exercise such as walking, jogging, running, running stairs, or hiking, etc. It is another object of the present invention that the tracking or monitoring device may have a power saving mode within to only monitor the held weight at the beginning of each arm movement, and then go into a sleep mode awakening only when the motion or continuous movement is altered or changed in such a way that it signifies the possible addition or subtraction of the held weight. For example, an individual starts to walk with one pound of held weight and is performing bicep curls to warm up their upper body, so the sensor initially tracks the one pound and then goes into sleep mode. After a few minutes the individual stops arm movements to add another weight segment or insert increasing the held weight to two pounds, so the tracking system is wakened by the sensors that identified a break in the movements, triggering the reader or scanner to check for a weight adjustment and therefore identifies the increase in held weight for all future arm movements until another break in movement occurs and so on. It is another object of the present invention that the digital body display can teach and help users develop an exercise routine by a simple user friendly mode in the monitoring device, smart phone, tablet, laptop or computer that is linked to the user's profile and history. For example, if a user wishes to work on training his or her triceps, the user would simply open the training mode on the device and point or tap the specific muscle or muscle group on the digital body display, then the digital body would offer several arm movements during aerobic exercise that would target the specific region identified. In yet another object of the present invention, small locking light units each powered by a battery may be specifically designed to attach to the ends of each weight unit by use of a screw system, magnet, or other friction locking method to illuminate the road or pathway, signaling to oncoming traffic, or others that an individual is present on the road or pathway at night or in the early morning when it is dark.

BRIEF DESCRIPTION OF THE DRAWINGS

To further clarify the above, other advantages and features of the present invention, a more particular description of the invention will be rendered by reference to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE INVENTION

Figure 1:
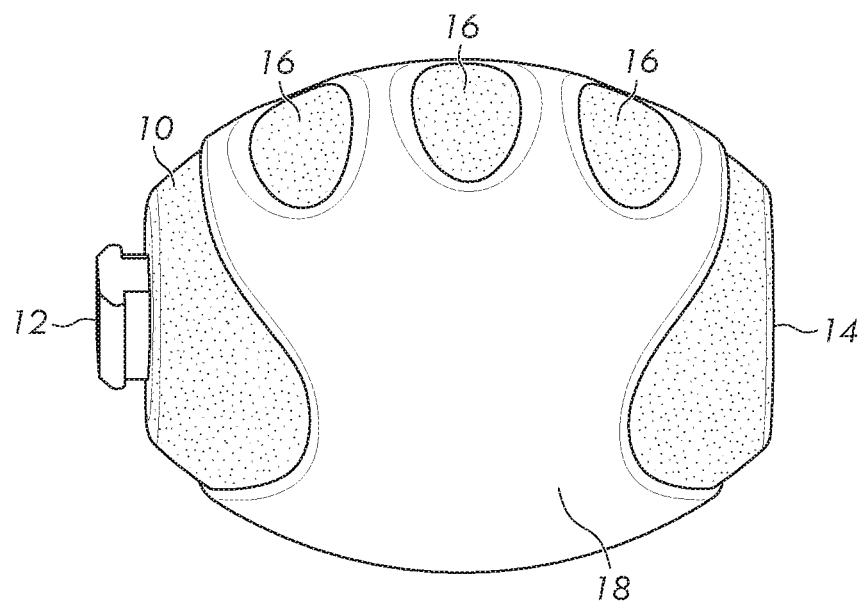
FIG. 1 is an isometric view of a modular weight unit in accordance with the present invention.

The foregoing and other objects, features, and advantages of the present invention will best be understood from the following description, the appended claims, and the accompanying drawings in which;

FIG. 1 is an isometric view illustrating a hand held modular weight unit 10. The modular weight unit includes several preferred embodiments including: the handheld weight unit's interlocking features 12, and 14, a set of ergonomic finger grips 16, and a rubber sleeve or griping cover 18. The two locking or latching devices, 12, and 14 are depicted here as a male and a female interlocking set capable of being twisted together into a locking or anchoring position to hold the two weight units together during use. Not depicted here is the potential use of one or more magnets to help lock the units together and hold them securely in place during use, as well as, allowing for the quick joining of the two weight units by magnetic force. The addition of the magnets may be a separate or secondary locking mechanism for security or may replace the male and female locking features entirely. The set of finger grips illustrated within as 16, and depicted as three individual finger indentations on the weight unit, 10, may be constructed with any number of finger grips from zero to 4 to align the weight unit in the center of the hand, and to promote the gentle holding thereof during use. The number, shape, and size of the finger grips will be determined by several contributing factors: the weight of the unit, the circumference and diameter of the weight unit, and the average size of the intended user's hand. Moreover, the inventor envisions that in order to satisfy the varying finger and hand sizes of users, it may be advantageous to have grip sizes, shapes, and counts that vary as well, depending on the fit and grip of the intended user. The rubber or silicone based sleeve or gripping glove, 18, is intended to assist users in achieving the exact fit and function desired as well as act as an anti-slip feature of the present invention, especially during prolonged exercise.

Similarly, to the finger grip variety, there may be many differing sizes, shapes and materials such as rubber gels, soft, or hard silicone materials to create a multitude of fits and grips for the user. In addition, a silicone gel sleeve may wrap around the entire weight unit, not pictured, allowing the user to custom mold his/her hand to the grip itself making the fit adjustable and soft to the touch.

Figure 2:
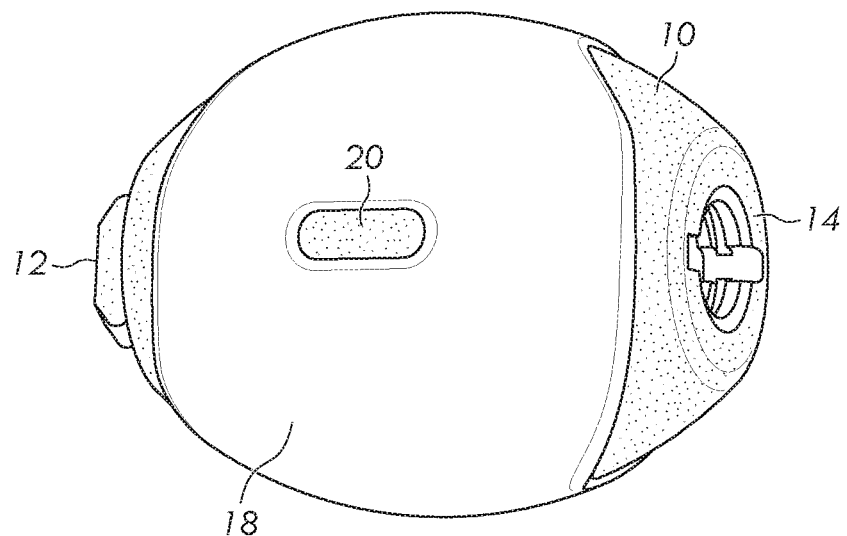
FIG. 2 is an additional isometric view of a modular weight unit from a rotated perspective.

FIG. 2 is an alternative isometric view of the present invention within FIG. 1 and highlights both the male and female locking mechanism, 12 and 14, as well as, the potential use of a RFID tag, 20, and placement thereof. A radius is applied to the edge of the male and female locking mechanism to ensure that users do not pinch their skin when joining the male locking feature 12 together with the female mechanism 14.

The weight of the unit, and material used will determine the differing diameters and lengths of the weight unit. Heavier weight units may have larger overall diameters or lengths but all will have identical locking mechanisms to ensure that varying sizes of weight units may be combined together without difficulty during exercise to alter the intensity of the exercise by changing the held weight. Additionally, light weight units may have a smaller circumference and length or the same circumference and length with a hollowed out center to achieve the desired weight and mass.

Figure 3:
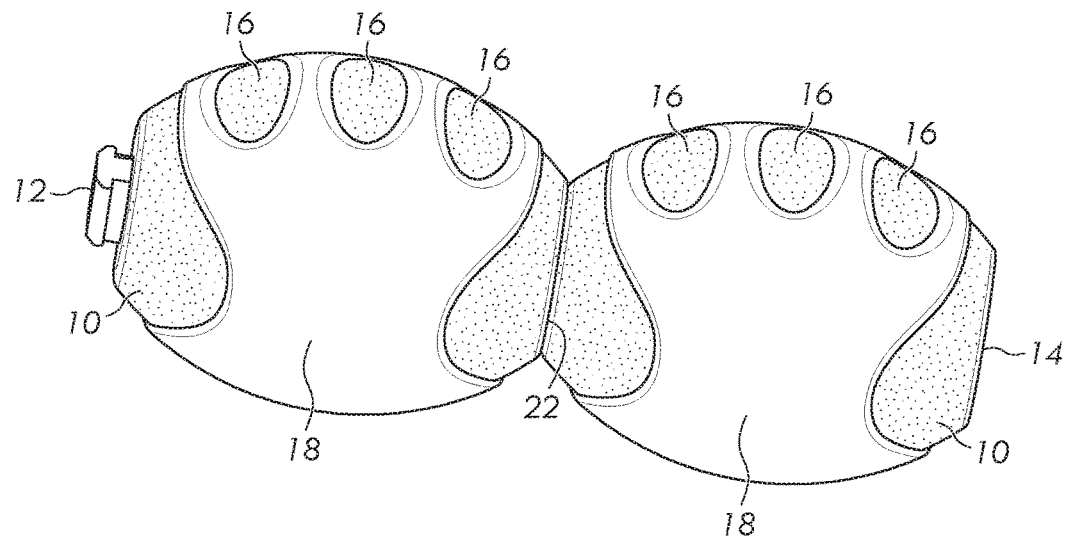
FIG. 3 is a perspective view of two modular weight units joined or locked together in a combined set.

FIG. 3 is an isometric view of the present invention described in FIG. 1 combined into a set. As previously described, the weight units are joined together by means of locking male mechanism 12, and female mechanism 14, locked together as 22. The weight units are rotated to create the locking or anchoring feature which may or may not be supported by the used of one or multiple magnets holding the weight units together by means of magnetic force.

Figure 4:
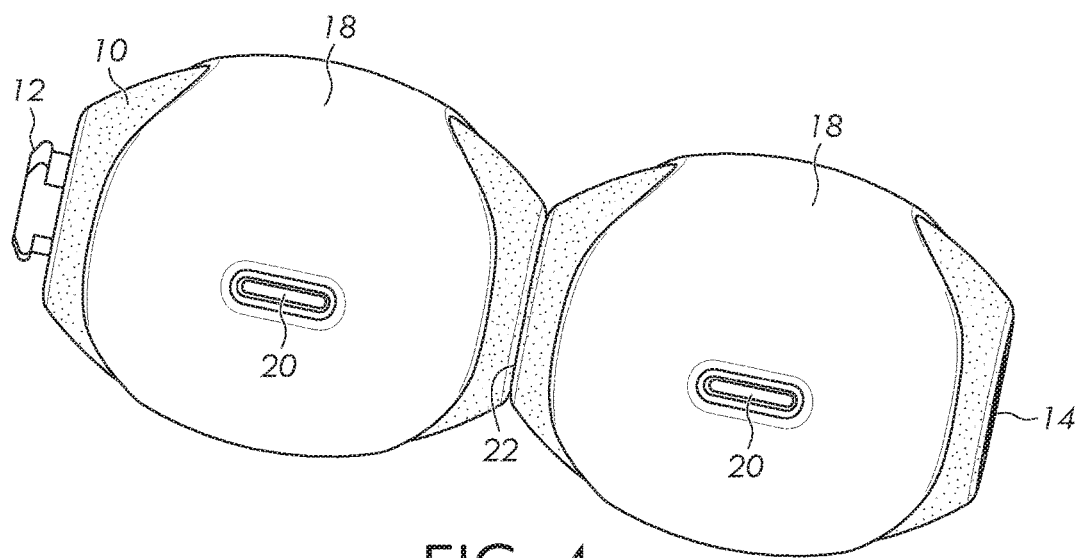
FIG. 4 is an additional perspective view of two modular weight units joined or locked together from a rotated perspective.

FIG. 4 is an alternative isometric view of the present invention depicting the back half of FIG. 3, highlighting each RFID tag, 20, on the identical weight units, 10. The RFID tags or chips are placed on the back side of the weight unit and opposite to the finger grips to allow for the ease of tracking of the weight units by a smart watch or other tracking device, 74.

Figure 5:
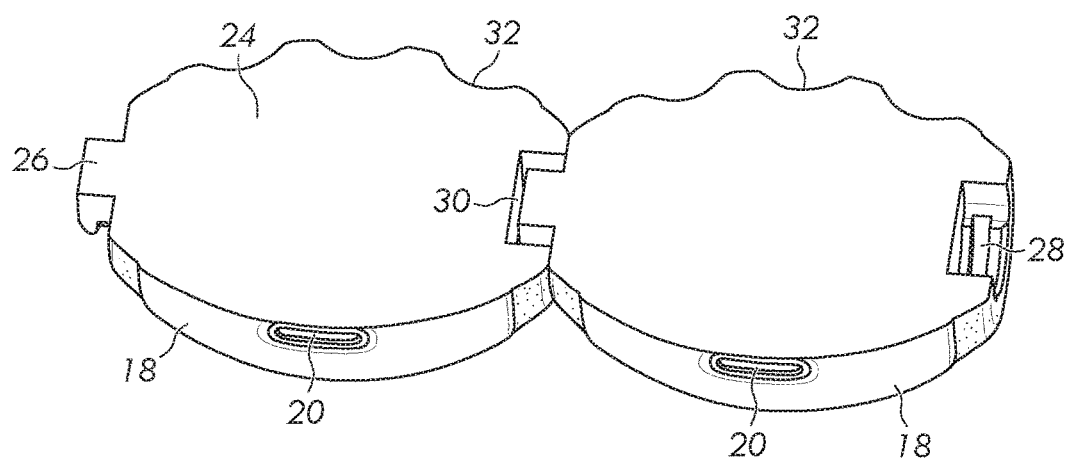
FIG. 5 is a cross section of the male and female interlocking embodiment method of the present invention.
Figure 6:
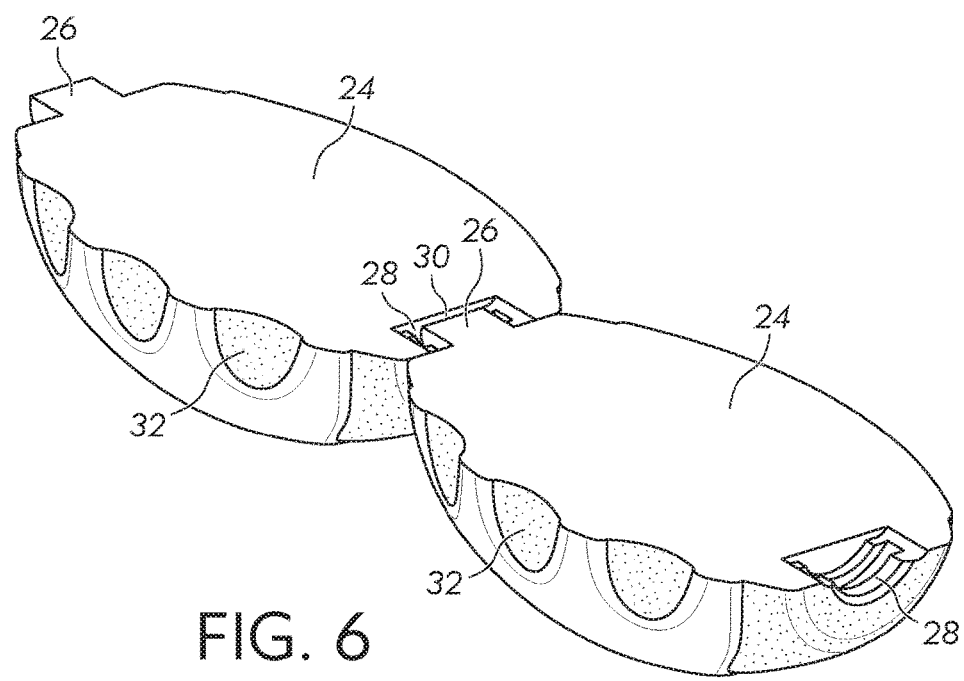
FIG. 6 is an alternative cross section of the male and female interlocking embodiment method of the present invention.

FIG. 5 and FIG. 6 are cross sectional views of the previous described joined set in FIG. 4, represented by 24 and highlighting the grooves within the female locking mechanism 28 as well as the male locking mechanism 26 and the union thereof as 30. Included within the cross sectional view is the finger grip indentations 32. The joined set pictured has a total of six combined finger grips giving the user a multitude of positions from which to grasp and hold the set in the hand during use. Not pictured is the option of using magnets to secure the lock during use or to replace the male and female locking mechanisms entirely.

Figure 7:
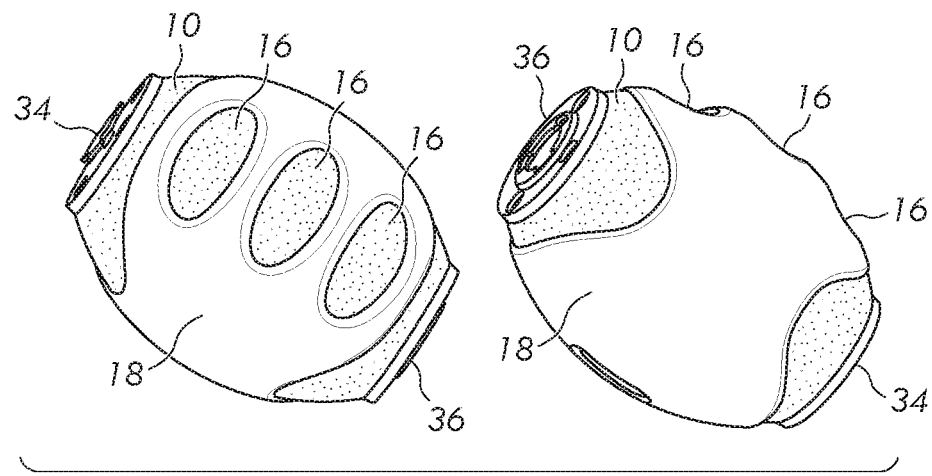
FIG. 7 is an alternative interlocking method featuring interlocking rigid structures of the present invention.

FIG. 7 is an isometric view of an alternative male and female locking mechanism, 34 and 36. The alternative locking mechanism could be more advantageous than the previous suggested solution referred to in FIGS. 1, 2, AND 3. The inventor wishes to identify that many possible interlocking methods exist to join like weight units together and one could argue the benefits and advantages of each; however, the present invention exists not solely on one or two methods of joining weight units together, but rather as a multitude of features and benefits that allow for increasing or decreasing the intensity of held palm centered weight with upper body exercises during aerobic activity. The inventor also envisions a locking mechanism, not pictured here, with a hidden male feature that is flipped out from the weight unit and inserted into a female locking mechanism when joining weight units. Such a system or combination could be more advantageous as it may help to reduce interference from the male locking feature during use with external parts such as headphone wires.

Figure 8:
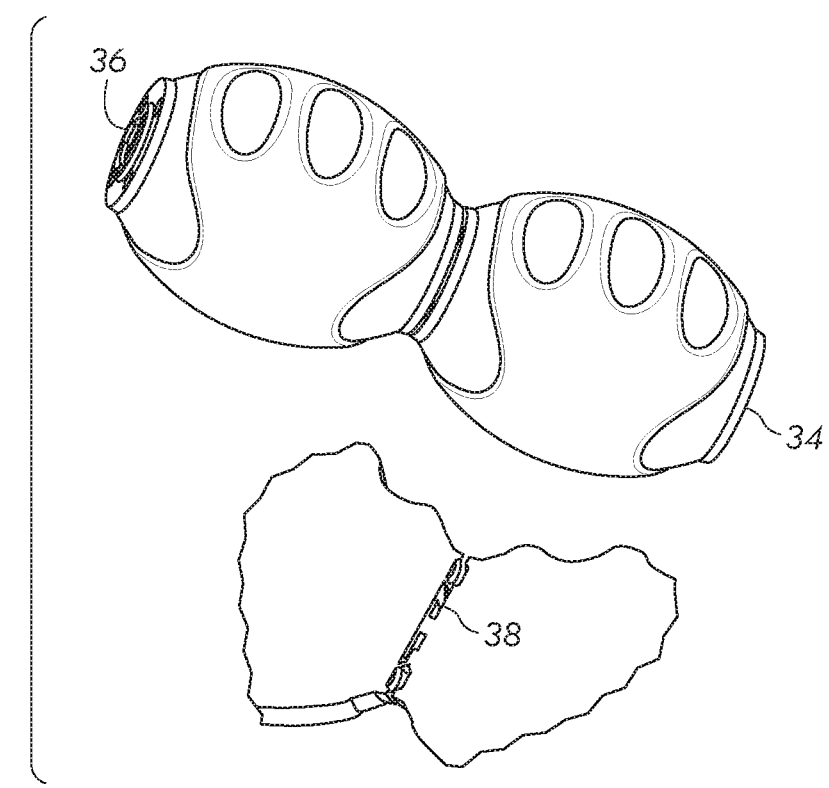
FIG. 8 is both a perspective view of an alternative interlocking weight unit and a close up of an alternative interlocking method featuring interlocking rigid structures of the present invention.

FIG. 8 is both an isometric view and a cross sectional view of the additional locking mechanism example described above and identified as the male locking mechanism 34, the female locking mechanism 36, and the joining of the two as 38.

Figure 9:
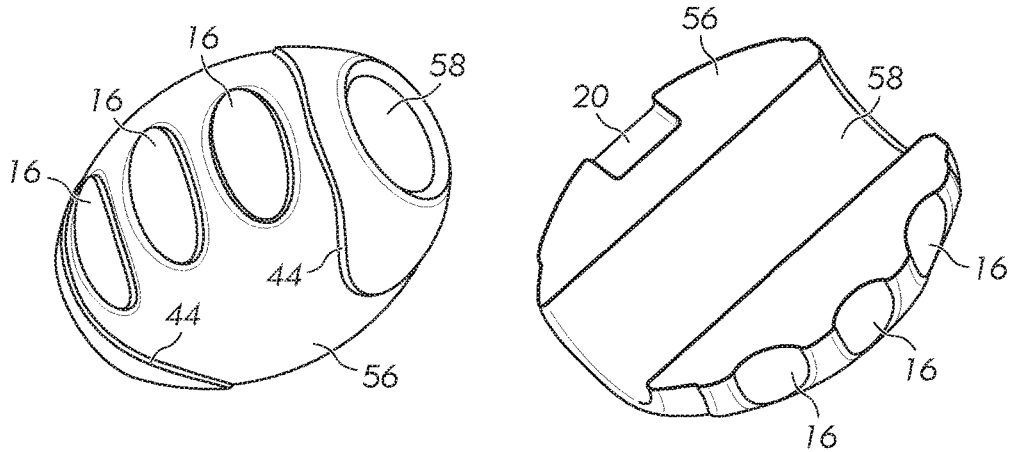
FIG. 9 is both a perspective view of an alternative weight unit shell and a cross sectional view of the alternative preferred embodiment of the present invention.

FIG. 9 is a both an isometric view and a cross sectional view of an additional embodiment of the present invention in which weight may be increased or decreased while centered in the palm of the hand during aerobic exercise by use of a master shell weight unit 56 and insert weight segments. Previously described features and elements are continued within the master shell weight unit and insert solution: finger grips 16, and RFID tag 20. The insert weight segment is inserted into the master shell weight unit by means of a center slot or tube 58. The insert weight segment may be locked or anchored into place during use to increase held weight during exercise. The center tube is best illustrated by the cross section view of the master weight unit 56. Weight inserts are cylinder in nature and therefore easily stored on the body by means of a weight belt, vest, arm band or other method previously discussed. Additionally, this design highlights a wave or raised ridge or line element on the outer portion of the master weight unit to hold the grip sleeve in place during use 44. The weight shell center core may be filled with alternative objects other than a weight insert. For example, a cylinder holding a car key, house key, or a tube of pepper spray may be advantageous for individuals who do not wish to run or walk with a belt or vest holding such items and therefore need a secure location to place these valued objects (not pictured).

Figure 10:
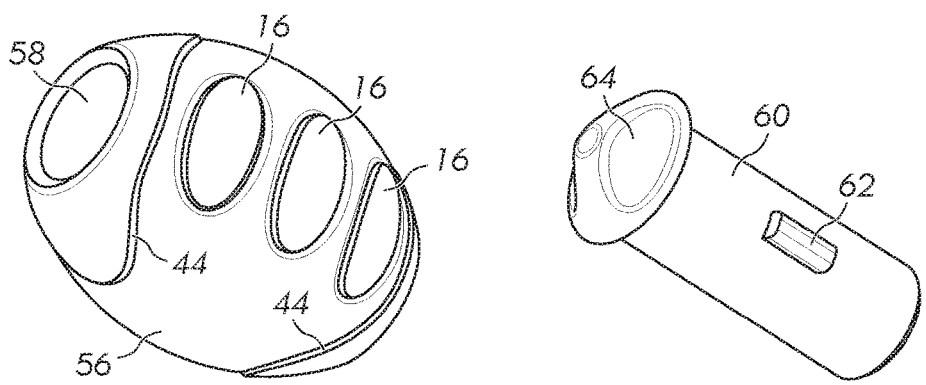
FIG. 10 is a perspective view of both the shell weight unit and matching insert of the alternative preferred embodiment of the present invention.

FIG. 10 is an isometric view of both the weight unit shell and the weight unit insert separate, 56 and 60 respectively. In the present view the weight unit insert is identical in length of the insert tube creating a flush end. It is anchored into place by means of twisting or locking the weight insert male feature 62 into a groove or notch located within the master weight shell, not pictured. The weight unit insert has a pointed finger grip head which allows for ease of insertion and providing gripping points from which to twist or spin the weight unit insert into the locking or anchoring position. Additional methods of locking or anchoring the insert weight into the weight shell can be imagined and several examples will be referenced below in FIG. 11.

Figure 11:
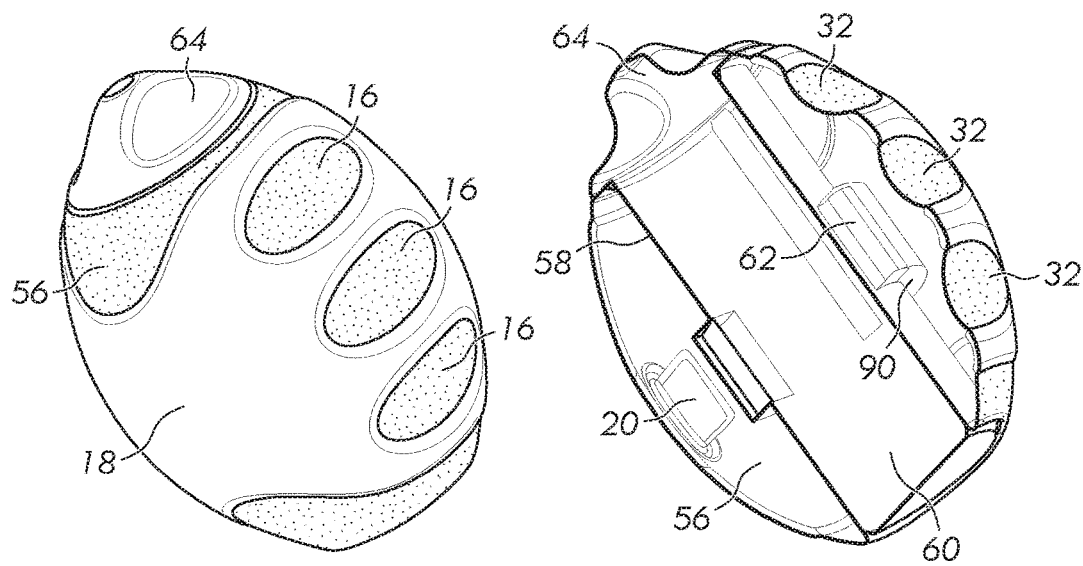
FIG. 11 is a perspective view of the shell weight unit with matching insert within, and a cross section view of the weight unit and insert as a combined set of the present invention.

FIG. 11 is both an isometric view of the weight shell unit and the weight unit insert combined, as well as, a cross section view of the two combined. Depicted in the isometric view are elements previously discussed and referenced as preferred embodiments of the present invention: 16, 18, 20, and 32. Considering the nature of the tube and insert solution, the inventor can imagine many possibilities of locking or anchoring the weight insert segment into the master shell tube such as: a screw and thread system at either ends of the tube and insert, a magnetic core or ring securing the weight within the shell, a magnet or ring on the underneath side of the head of the insert coming in contact with a steel plate or ring, an interlocking edge or hook at any point of the tube or insert that locks or links them together, and a multitude of other methods using locking pins, pressure balls and sockets, latches, push or sliding locking features, or other friction locking mechanisms. The ability to add and remove weight with ease during aerobic exercise is critical to maximize the intensity of the exercises performed during aerobic activity.

Figure 12:
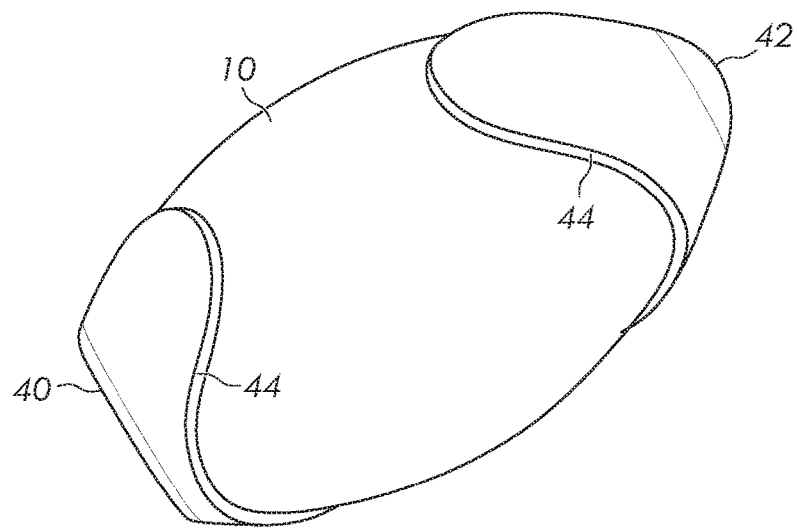
FIG. 12 is a perspective view of an alternative singular non-interlocking weight unit with a flat end and no finger grips.

FIG. 12 is an isometric view of a solid weight unit 10, with previously mentioned wave grooves or lines 44, with a flat end little finger rest 40, and a rounded thumb rest at the head of the weight unit 42. Many individuals may not desire the altering weight segments and prefer the traditional singular weight measurement when performing exercises during aerobic activity; however, they would greatly benefit from the use of a palm centered weight unit that does not exceed the circumference of their hand for all of the previously stated reasons when compared to traditional light weight dumbbells, or light weight adjustable dumbbells. The weight unit is specifically designed to be ergonomically held in the center of the palm or hand and takes special attention to the flexibility of not having finger grips cut into the weight's body as this design is to accommodate many finger shapes and sizes as well as a sleeve or glove.

Figure 13:
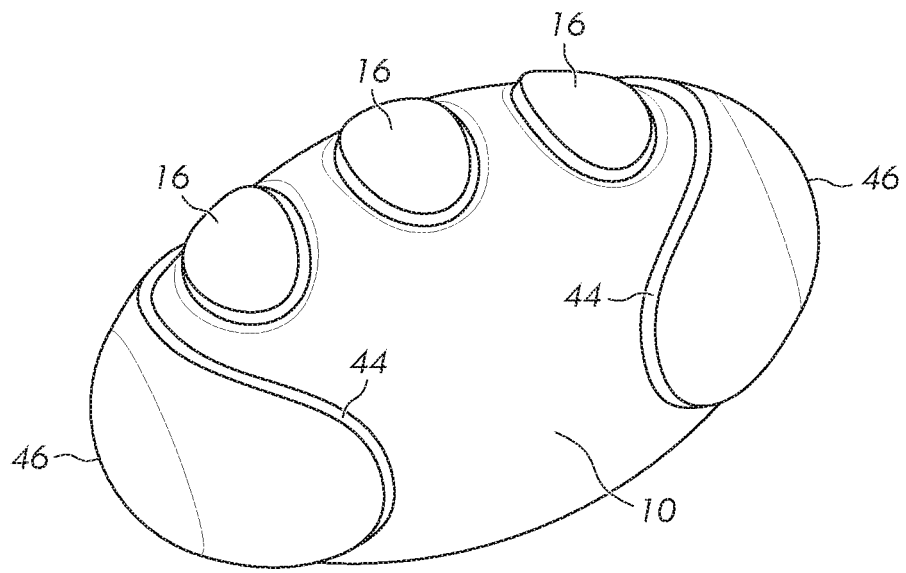
FIG. 13 is a perspective view of an additional singular non-interlocking weight unit with rounded ends and finger grips.

FIG. 13 is an isometric view of a solid weight unit 10, with previous mentioned preferred embodiments 16, and 44 with a new rounded end feature 46. In order to achieve certain desired weights, in a solid unit configuration, special shapes are needed to increase the volume or mass of the palm centered weight unit without exceeding the normal circumference range of the intended user's hand. The largest and heaviest weight units may slightly exceed the intended user's hand circumference and therefore a rounded end may be advantageous to allow for the desired volume with only the smallest amount of weight unit extending past the intended user's hand circumference. During prolonged aerobic exercise, the rounded ends also prevent the aforementioned shortcomings of prior art coming in contact with the body, or other objects such as treadmill side rails, electronic wires, or other items carried on the body such as water bottles or cell phones.

Figure 14:
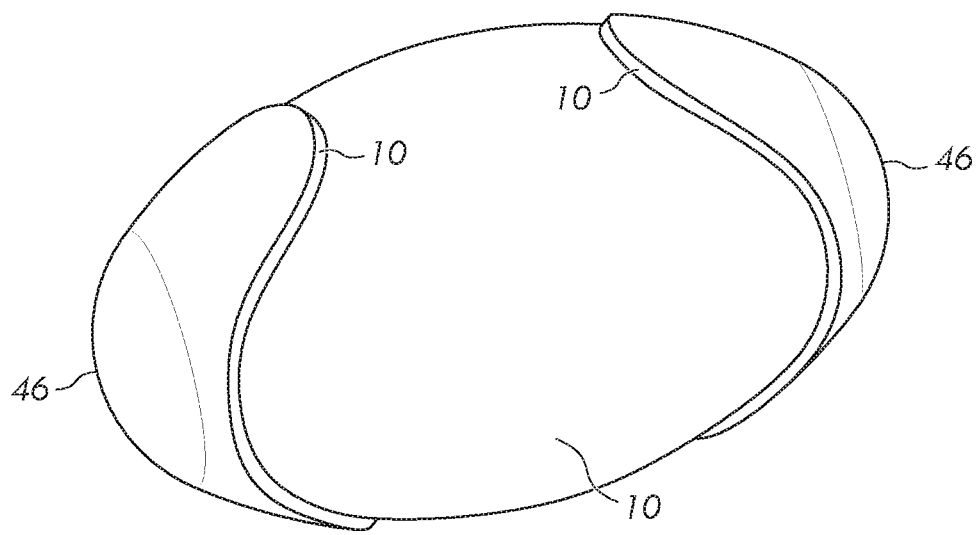
FIG. 14 is a perspective view of an alternative singular non-interlocking weight unit with rounded ends and without finger grips.

FIG. 14 is a similar isometric view of FIG. 13 without the finger grips 16. The heavier the weight units become, the more varying the hand or finger positioning may become. Therefore, it may be more advantageous to have a rounded end feature 46 without any finger grips, allowing the users to position their fingers at the most functional places to hold the weight comfortably in the center of the hand during prolonged exercise. In addition, users may want to rotate the weight units around in their hands during prolonged use, therefore making a blank finger grip unit most advantageous when compared to those with restrictive pre-molded finger settings.

Figure 15:
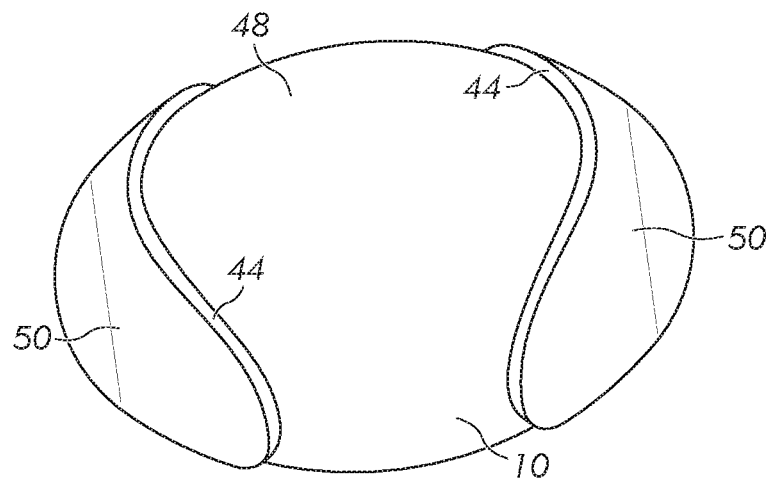
FIG. 15 is a perspective view of an additional alternative singular non-interlocking weight unit with a rounded body and without finger grips.

FIG. 15 is a similar isometric view of FIG. 14 with the addition of a large rounded body 48, and large rounded ends 50. Considering most individuals have unique grips and preferences when holding objects, it may also be advantageous for some users to have the option of carrying a weight unit with an increased midsection with larger rounded ends to achieve the desired volume to achieve a heavier weight unit.

Figure 16:
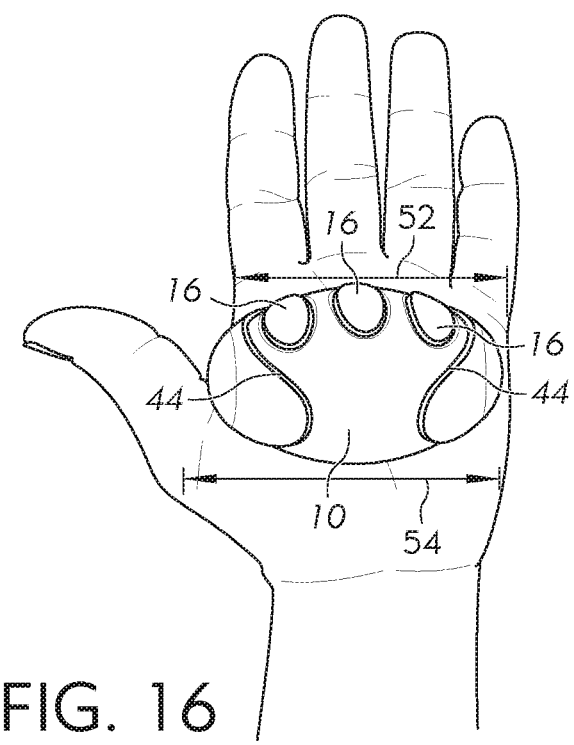
FIG. 16 is a perspective view of the modular weight unit held centered in the palm of the hand in a singular unit use, non-interlocking weight unit.

FIG. 16 is a top view of the solid weight unit exhibited in FIG. 13 in an open hand. The weight unit 10, with previously identified preferred embodiments 16 and 44, is depicted as being held across the open hand of an intended user. The open hand circumference at the middle portion of the palm, 52, is smaller than the circumference at the base of the hand which includes the thumb, and outer muscle portion of the hand, 54. Therefore, both dimensions must be considered when developing the correct diameter and circumference of the weight unit. It is most advantageous, for previously mentioned reasons, that the outer most portion of the weight unit must not exceed the total length of the base portion of the palm, 54, but yet lay comfortably across the narrow portion of the palm 52.

Figure 17:
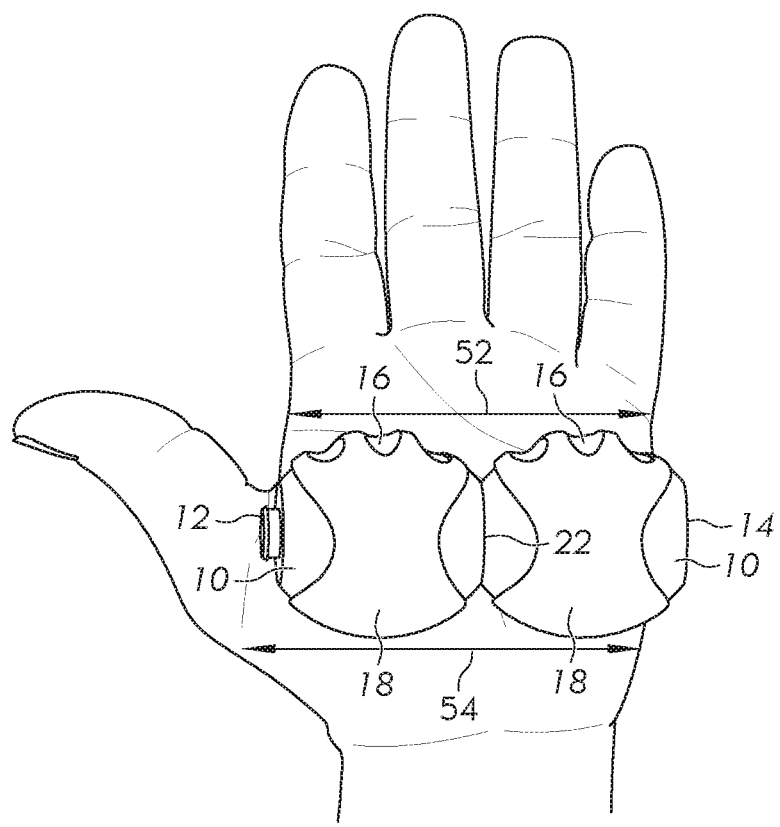
FIG. 17 is a perspective view of the modular weight unit held centered in the palm of the hand in a combined set.

FIG. 17 is a top view of the joined modular weight unit set exhibited in FIG. 3 in an open hand. The modular weight unit set of 10 and 22, with previously identified preferred embodiments 12, 14, 16, and 18, is depicted as being held across the open hand of an intended user. As previously mentioned above, it is most advantageous when joined weight sets do not exceed the circumference of the open hand 52 and fit comfortably in the palm of the hand 54.

Figure 18:
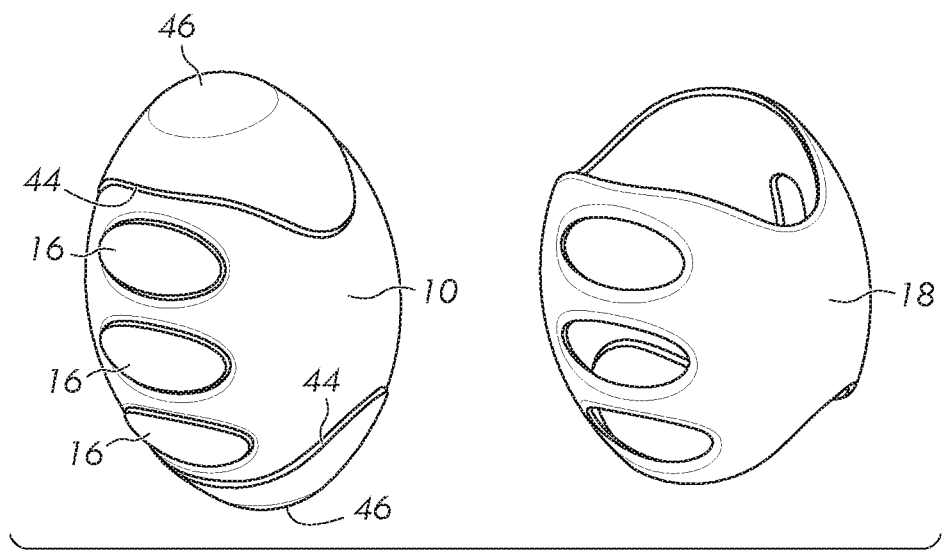
FIG. 18 is a perspective view of the modular weight unit and the rubber grip or glove of the modular weight separately.

FIG. 18 is an isometric view of the weight unit exhibited in FIG. 13, as 10, and a second isometric view of its corresponding sleeve or glove grip exhibited in FIG. 1, as 18. The single weight unit 10 with its previously identified preferred embodiments 16, 44, and 46, where 44 is the locking or fitting ring for the sleeve or grip glove, 18. The flexible but durable nature of the sleeve or grip glove 18 allows for the ease of application onto the weight unit 10. Users simply pull the sleeve or grip glove around the weight unit and then slide it into place, snug against the wave or line, 44, securing it in place during use. As previously noted, the sleeve or grip glove may be made from varying materials and thicknesses of materials to provide users with a more adjustable fit and holding of the weight unit in the palm of the hand. In addition, the sleeve can be hand washed with soap and water to clean the sleeve or grip glove after use.

Figure 19:
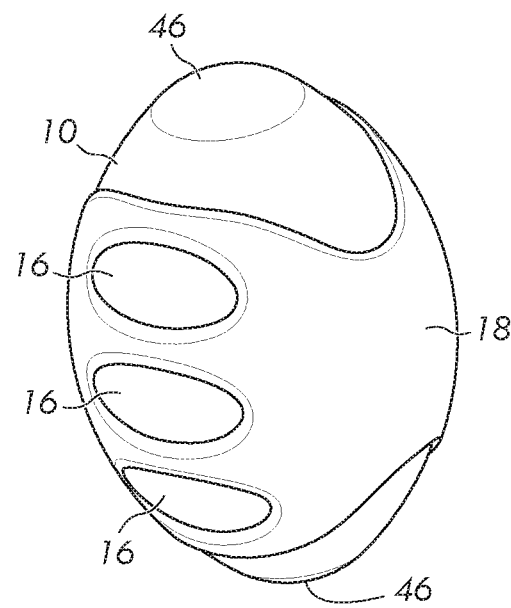
FIG. 19 is a perspective view of the modular weight unit and the rubber grip or glove of the modular weight combined.

FIG. 19 is an isometric view of the combined two elements identified and described in FIG. 18.

Figure 20:
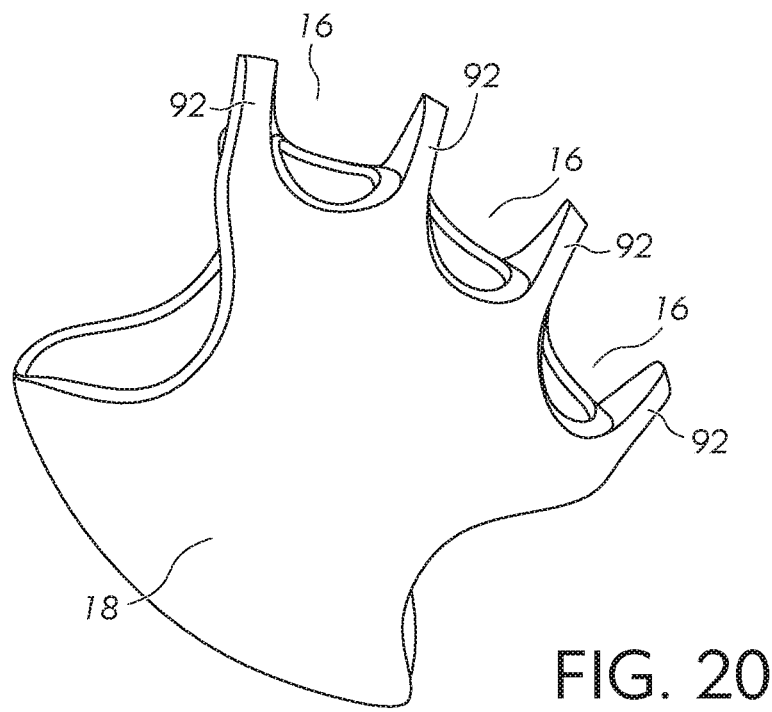
FIG. 20 is a perspective view of the weight unit sleeve with longer extended finger grips.

FIG. 20 is an isometric view of the weight sleeve, 18 with extended finger grips, 92 and finger holds 16. The extended finger grips 92 may be more advantageous for some users when performing upper body movements during prolonged aerobic exercise, as the taller grips allow for easier holding of the weight unit in the hand. Any number of taller finger grips may be added to the sleeve to create the desired fit. In addition, the sleeve may also wrap the entire grouping of fingers, enclose any combination of fingers, or enclose any one finger to create a more secure joining of the weight unit and the hand, not pictured.

Figure 21:
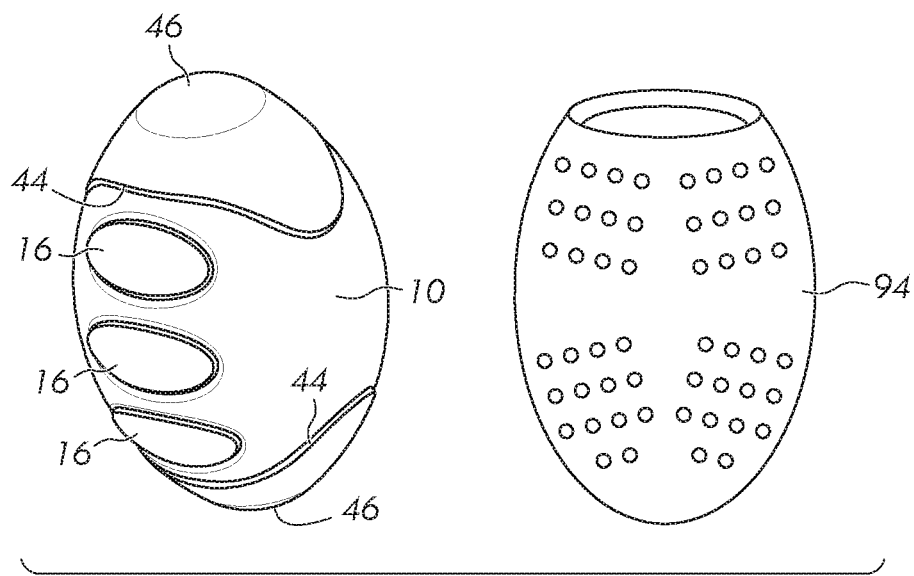
FIG. 21 is a perspective view of the weight unit sleeve with a malleable soft grip sleeve.

FIG. 21 is an isometric view of the weight unit 10 with previously identified preferred embodiments, 16, 44, 46, and a malleable weight sleeve, 94. The malleable sleeve is intended to be squeezed in the hand and manipulated by the fingers, ostensibly to either help relieve stress and muscle tension or to exercise the muscles of the hand during aerobic activity in combination with held weight unit 10. Material can range from closed-cell polyurethane foam rubber, to a soft aerated or bubbled silicone, to a gel of varying densities inside a rubber or cloth skin. All of these possible materials are intended to provide a resistance to the hand during a squeezing or gripping hand motion. This preferred embodiment is particularly advantageous for those who wish to provide stress or muscle tension relieve in combination with aerobic exercise.

Figure 22:
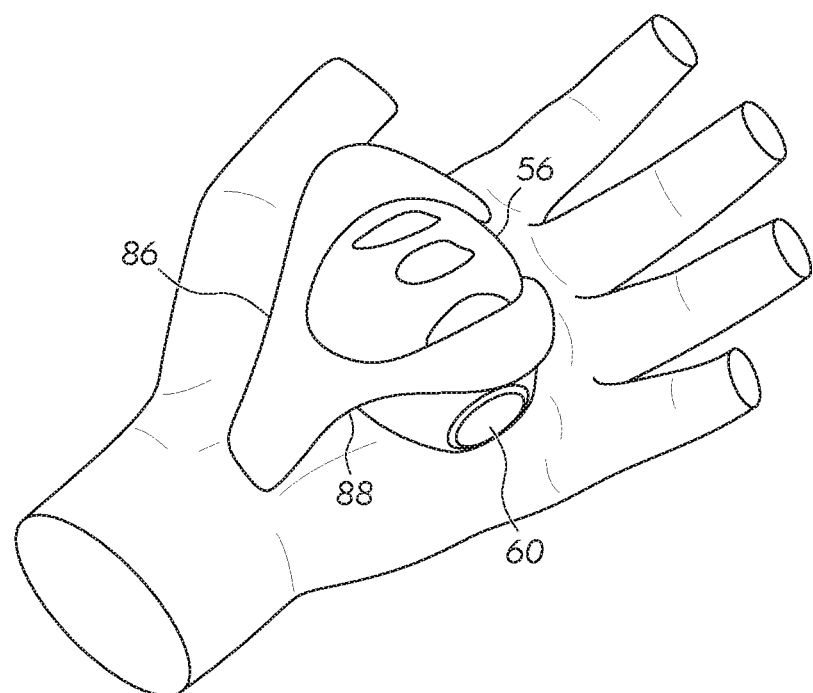
FIG. 22 is a perspective view of a glove with a weight unit pocket to hold the weight unit in place during high frequency, fast upper body movements.

FIG. 22 is an isometric view of a glove complete with weight unit pocket, 86, and 88. As previously identified, fast arm movements may require users to secure the weight units by means of straps, bands, or gloves. This glove example highlights a pocket where the weight unit is secured and housed during exercise, preventing the weight unit from falling or dropping during use. Similar pockets with VELCRO™ hook-and-loop fastener strapping may be just as effective as the glove example shown, but considerably more adjustable to hand fit.

Figure 23:
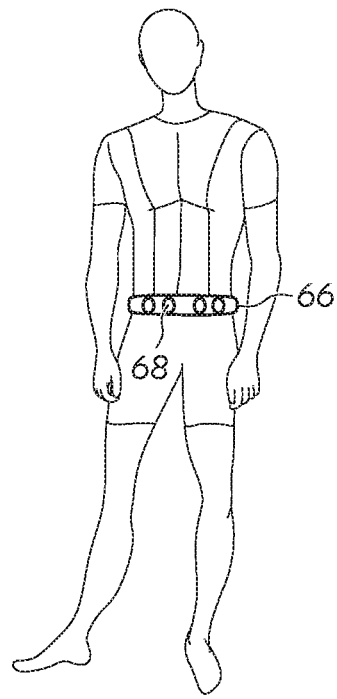
FIG. 23 is a perspective view of the modular weight unit stored on the body by use of a waist belt.

FIG. 23 is an isometric view of a waist belt, 66, where weight units or inserts can be stored and housed in pockets, 68, during aerobic exercise until needed by the user to increase held weight or reduce held weight by storing weight units or inserts on the core of the body. Similar devices may be constructed with additional features such as a water bottle holder, a pocket for keys, a cell phone holder, etc.

Figure 24:
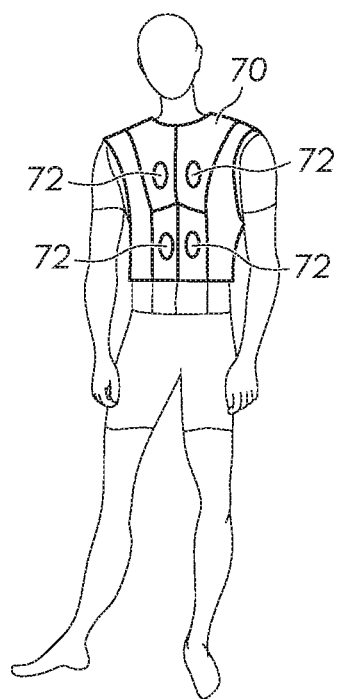
FIG. 24 is a perspective view of the modular weight unit stored on the body by use of a vest.

FIG. 24 is similar in nature to FIG. 21 depicting a weight storage vest, 70, with storage pockets, 72, for the storing of weight units and inserts or both during aerobic exercise until needed by the user.

Figure 25:
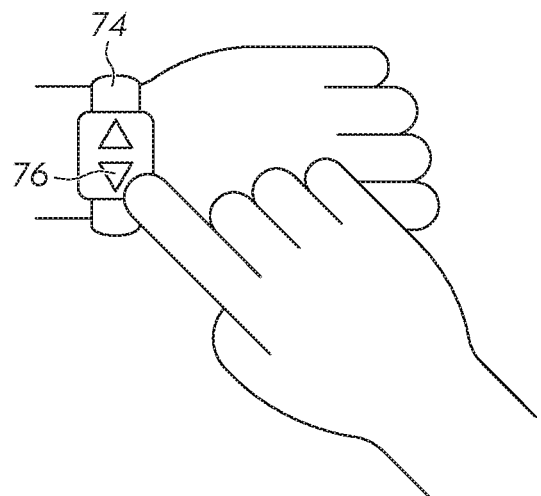
FIGS. 25, 26 and 27 respectively are perspective views of various modular weight units being tracked or monitored by a worn device by use of a manual, audio, and automated sensor tracking RFID tag method.

FIG. 25 is an isometric view of a worn wrist tracking device, 74, and an example of a manual touch screen, 76, within to enter the changes in held weight into the tracking device during aerobic exercise. In addition to a touch screen method of inputting held weight values during exercise, other methods may be utilized such as a scrolling ball, push button, or tap bars to identify the starting weight and changes made throughout physical activity. As previously discussed the ability to simply and easily track held weight values during physical activity is crucial to monitor and track the exertion and intensity of the workout both during and after exercise, as a summary.

Figure 26:
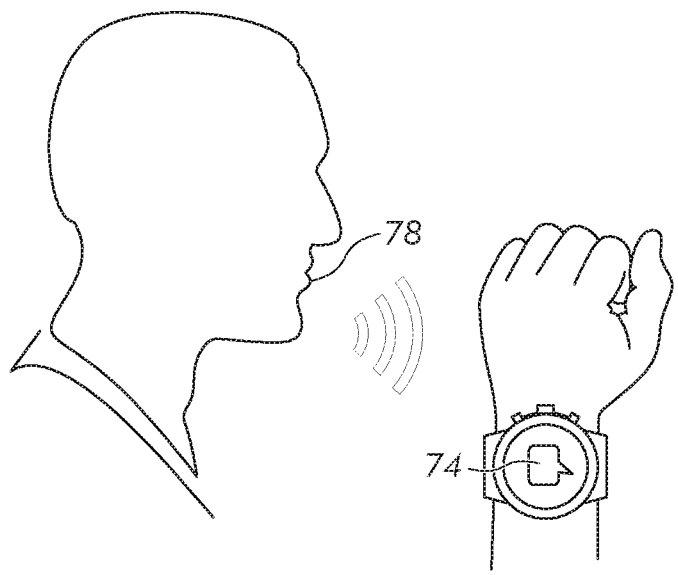

FIG. 26 is an isometric view of a worn wrist tracking device, 74, and an example of changing held weight values by means of voice, 78. It may be more advantageous for some individuals to speak directly into the tracking device to input varying held weight during aerobic exercise, for all the previously noted reasons.

Figure 27:
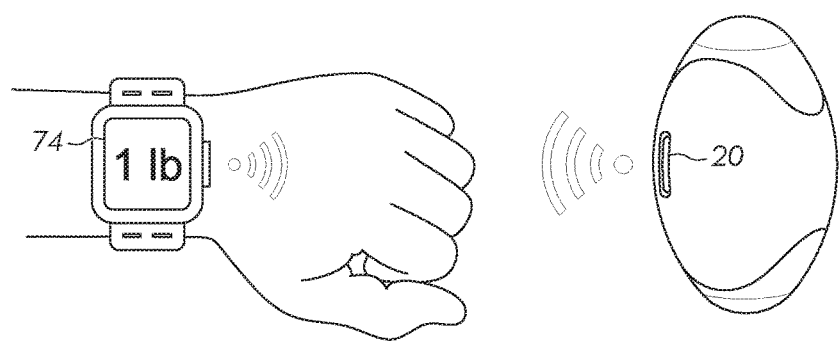

FIG. 27 is a similar view of FIGS. 23 and 24 but highlights the use of the RFID tag to track the varying held weight during physical exercise. Although more expensive to implement, the RFID tag system is a failsafe way to track held weight without the user having to alter their exercise form to manually input the change in weight. The combination of multiple RFID tags to create a new measure of weight would require a tracking or monitoring device capable of reading multiple RFID tags simultaneously.

Several established methods of determining calorie burn based on heart rate and other contributing factors may be used. Any of these established methods may be used to track and monitor the user's calorie burn rate during aerobic activity through monitoring devices such as smart watches or heart rate monitors worn on the wrist or forearm as previously mentioned. User's that wish to track the intensity of their workout with the varying held weight against aerobic exercise without will need to create a base line from which the noted methods may be used to evaluate and summarize the differing intensities of workout. These methods of tracking calorie burn and identifying the intensity of exercise may also be used to monitor the user's level of physical fitness, as well as, notify the user when their level of intensity has flat lined or created a new normal level of exertion. This is critical to identify to the user when it is time to increase the held weight, thus creating a higher level of intensity during aerobic exercise.

Calorie Burn Equations
Harris Benedict Method $$BMR\ Men := 66 + (6.23 \times weight\ in\ pounds) + (12.7 \times height\ in\ inches)(6.8 \times age)$$

$$BMR\ Women := 655 + (4.35 \times weight\ in\ pounds) + (4.7 \times height\ in\ inches)(4.7 \times age)$$

The Harris-Benedict equations revised by Mifflin and St Jeor in 1990:

$$Men\ BMR = (10 \times weight\ in\ kg) + (6,25 \times height\ in\ cm) - (5 \times age\ in\ years) + 5$$

$$Women\ BMR = (10 \times weight\ in\ kg) + (6,25 \times height\ in\ cm) - (5 \times age\ in\ years) - 161$$

C=(0.4472×H−0.05741×W+0.074×A−20.4022)×T/4.184. C is the number of calories that you burned, H is your average heart rate, W is your weight, A is your age and T is the length of your exercise session in minutes. Assume that you're a 28-year-old female weighing 146 pounds. Your average heart rate during an exercise session that lasted 36 minutes was 138 bpm. You burned C=(0.4472×138−0.05741×146+0.074×28−20.4022)×36/4.184=301 calories.

Katch & McArdle Method $$BMR(Men+Women) = 370 + (21.6 * Lean\ Mass\ in\ kg)$$

$$Lean\ Mass = weight\ in\ kg - (weight\ in\ kg * body\ fat\ \%)$$

1 kg=2.2 pounds, so divide your weight by 2.2 to get your weight in kg

Figure 28:
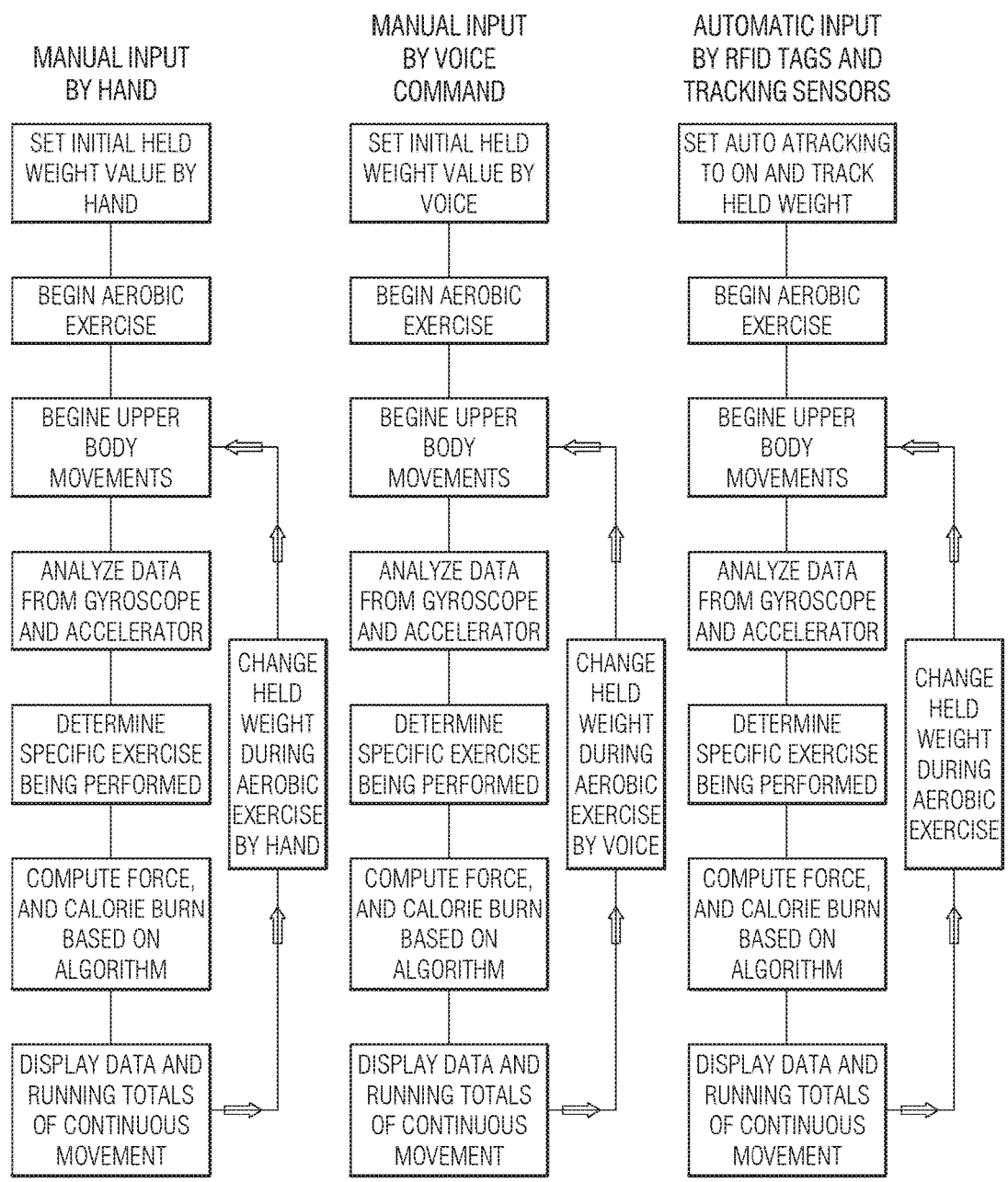
FIG. 28 is three flow diagrams showing the preferred methods of tracking and inputting held weight values of the present invention while tracking and monitoring upper body arm movements during aerobic exercise.

Activity Multiplier (Both HB+KA Method use same activity multiplier)
Little or No Exercise, Desk Job 1.2×BMR
Light Exercise, Sports 1 to 3 Times Per Week 1.375×BMR
Moderate Exercise, Sports 3 to 5 Times Per Week 1.55×BMR
Heavy Exercise, Sports 6 to 7 Times Per Week 1.725×BMR FIG. 28 has three separate flow chart examples, each depicting how the tracking and monitoring device might calculate and store data both inputted manually or automatically. The flow charts also depict how the tracking or monitoring device might use data from previously noted source FIG. 26 and calculate output and a work out summary of physical activity both continuously and after exercise.

Figure 29:
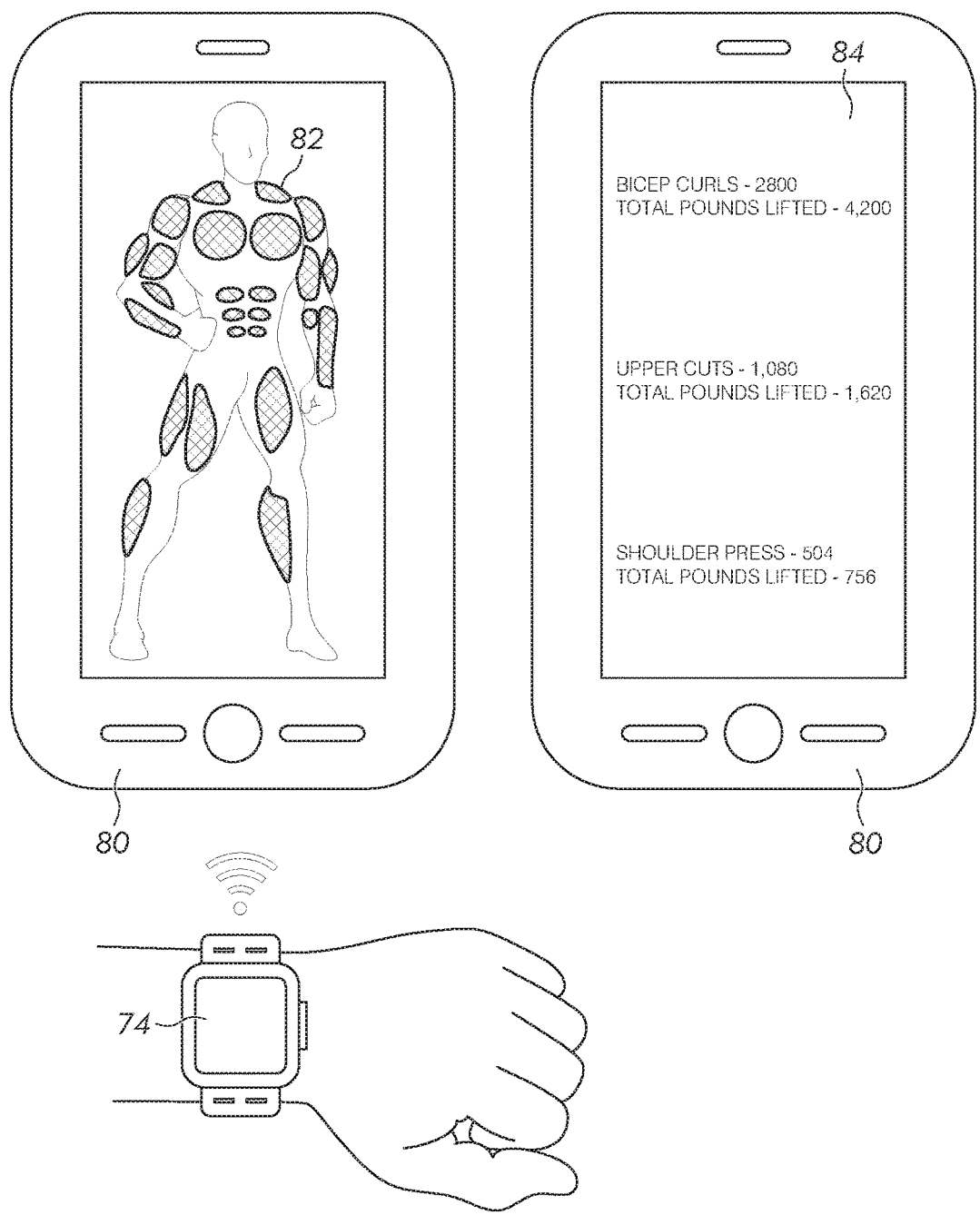
FIG. 29 is an example of the preferred embodiment of the present invention detailing a digital body display and data display example of the total body summary either during or after aerobic exercise on a smart phone, tablet or similar device.

FIG. 29 is an isometric view of a smart phone or tablet, 80, depicting two options of how to review the data and summary information, 82, 84. Information will be transferred from the smart watch, 74, to the tablet by means of a Bluetooth connection or other means of data transfer, wire, cable, etc. Many different formats may be available to choose from to view data summary. The first example is of a total digital, male or female body, 82, displaying the exertion and intensity of the muscle groups used during the period of exercise. The differing in intensity will be identified by a color; for example, red would hold a value of high intensity while green would hold the lowest value of intensity. By touching the muscle group, the user may pull up an alternative view highlighting the specific data generated by that individual muscle group. In addition to a summary page, the digital body can also be used in the training mode where users can identify a specific targeted area and review motions or exercises to target those areas. The second example shows a simple data sheet, 84, to review performance and summary of activity. Additional pages may show full history of exercises with held weight to track performance over a longer period of time to show improvement and strength building.

Activity summary could include but is not limited to:
1. Type of activity performed during aerobic activity—running, walking, hiking, etc.
2. Type of exercises performed during aerobic activity—bicep curls, shoulder press, chest squeeze, upper cuts, triceps extensions, etc.
3. Total amount of upper body exercises performed.
4. Total amount of steps or strides achieved during activity.
5. Total amount of miles achieved during aerobic activity.
6. Total amount of held weight by each exercise for the duration of the aerobic activity.
7. Total amount of held weight by duration of aerobic activity.

8. Total amount of held weight this week, month, and year.
9. Total amount of miles performed this week, month, and year.
10. Total calories burned during activity.
11. Total calories increased with the use of the weight units and exercises versus just aerobic activity alone.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

What is claimed is:

1. An exercise weight unit adapted to be hand held and palm-centered, comprising:
   an egg-shaped solid unit having first and second ends, a central portion, and a central axis between the first and second ends, wherein the central portion and first and second ends each have a diameter, and the diameter of the central portion is larger than the diameters of the first and second ends;
   a plurality of ergonomic finger grips attached to an outer surface of the egg-shaped solid unit in the central portion, and configured such that when a user holds the exercise weight unit in a hand of the user, one or more fingers of the hand of the user rest against one or more ergonomic finger grips of the plurality of ergonomic finger grips, and wherein the plurality of ergonomic finger grips are configured to align the exercise weight unit in a center of a palm of the hand; and
   a rubber sleeve wrapped around the exercise weight unit, wherein the rubber sleeve defines one or more openings adapted to respectfully receive the plurality of ergonomic finger grips.

2. The exercise weight unit of claim 1, further comprising:
   a wireless transceiver included in the egg-shaped solid unit configured to communicate with a separate computing device so the separate computing device can track movement of the exercise weight unit.

3. The exercise weight unit of claim 1, further comprising:
   a female interlocking mechanism at the first end and a male interlocking mechanism at the second end, thereby enabling the exercise weight unit to be interlocked at the first end or the second end with another exercise weight unit.

4. The exercise weight unit of claim 1, further comprising:
   a magnetic interlocking mechanism at the first and second ends, thereby enabling the exercise weight unit to be interlocked at the first end or the second end with another exercise weight unit.

5. The exercise weight unit of claim 1, further comprising hook and loop fasteners on the egg-shaped solid unit.

6. An ergonomic exercise weight unit adapted to be hand-held and palm-centered, comprising:
   an elongated substantially egg-shaped rubber outer shell having first and second ends, a central portion, and a central axis between the first and second ends, wherein the central portion has a diameter that is larger than a diameter of each of the first and second ends;
   a solid weight segment inside the elongated substantially egg-shaped rubber outer shell positioned along the central axis;
   a plurality of finger grips attached to an outer surface of the elongated substantially egg-shaped rubber outer shell in the central portion;
   a wireless transceiver included in the elongated substantially egg-shaped rubber outer shell configured to communicate with a separate computing device so the separate computing device can track movements of the ergonomic exercise weight unit;
   a gyroscope sensor included in the elongated substantially egg-shaped rubber outer shell; and
   a female interlocking mechanism at the first end and a male interlocking mechanism at the second end, thereby enabling the ergonomic exercise weight unit to be interlocked at the first end or the second end with another ergonomic exercise weight unit.

\* \* \* \* \*